United States Patent [19]

Smith

[11] Patent Number: 5,797,904
[45] Date of Patent: Aug. 25, 1998

[54] MULTI-PROBE BLEND ELECTROLYSIS MACHINE

[75] Inventor: Margaret M. Smith, Reno, Nev.

[73] Assignee: Clareblend, Inc., Sparks, Nev.

[21] Appl. No.: 774,962

[22] Filed: Dec. 27, 1996

[51] Int. Cl.[6] .................................................. A61B 17/41
[52] U.S. Cl. ........................................... 606/36; 606/44
[58] Field of Search ................................. 606/36, 43, 44; 607/75

[56] References Cited

U.S. PATENT DOCUMENTS

| | | | |
|---|---|---|---|
| 1,781,362 | 11/1930 | Brigida | 606/44 |
| 1,906,802 | 5/1933 | Miller | 606/36 |
| 3,815,603 | 6/1974 | Sramek | 606/36 |
| 4,155,363 | 5/1979 | Letchworth et al. | 606/36 |
| 4,598,709 | 7/1986 | Smith et al. | 606/44 |
| 5,514,167 | 5/1996 | Smith et al. | 607/75 |

*Primary Examiner*—Lee S. Cohen
*Attorney, Agent, or Firm*—Jack C. Munro

[57] ABSTRACT

An electrolysis machine which uses a plurality of probes each of which is to be insertable in conjunction with a hair follicle to effect removing of a hair. The probes are mounted on an arm unit which is adjustably movable to a multitude of different positions relative to a base unit which is fixedly located on a supporting surface. An electrolysis machine produces both direct current and a radio frequency with the user being able to select just the direct current or the direct current combined with the radio frequency in the performing of the destruction of the hair. The current emitted to effect the destruction of the hair is slowly raised (over a two second time period) to a level that is preset by the operator.

6 Claims, 8 Drawing Sheets

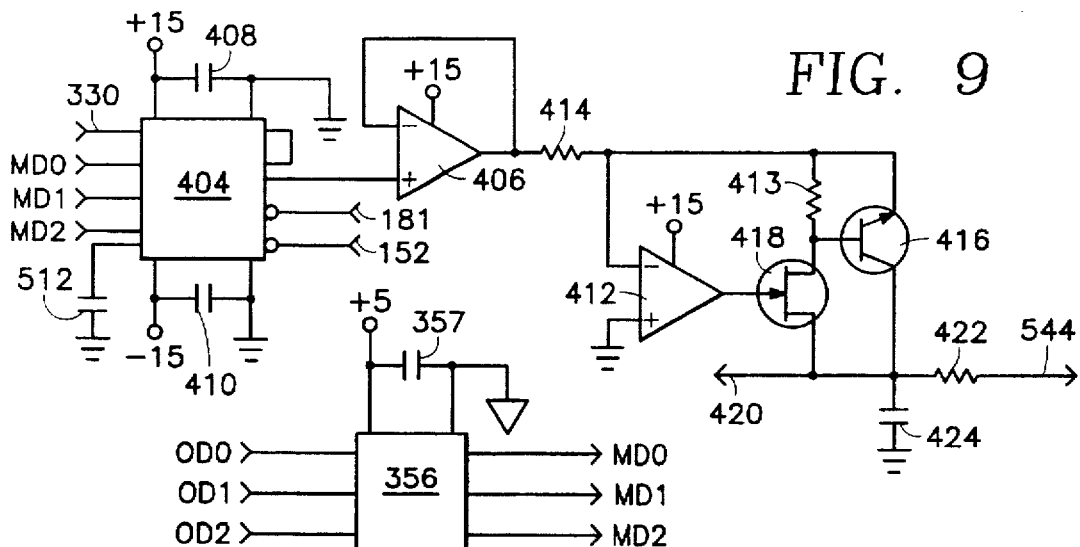
FIG. 9
FIG. 12
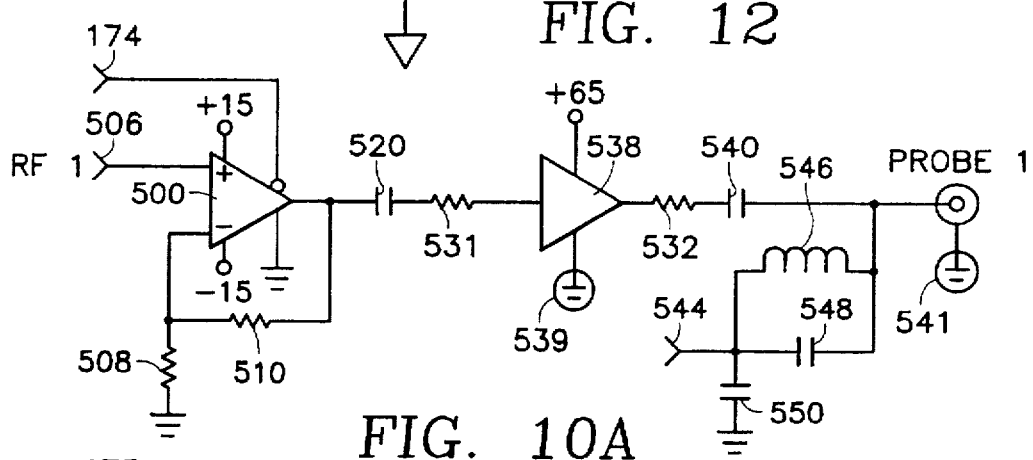
FIG. 10A
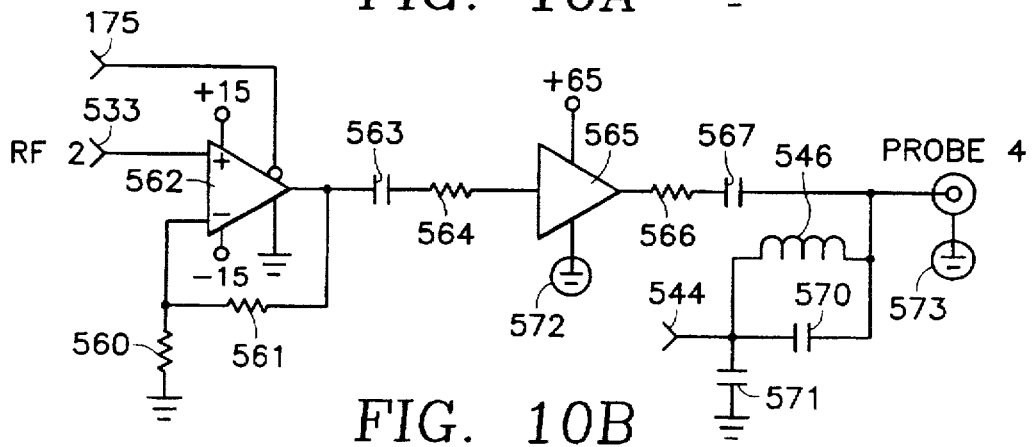
FIG. 10B

MULTI-PROBE BLEND ELECTROLYSIS MACHINE

BACKGROUND OF THE INVENTION

1) Field of the Invention

The field of this invention relates to electrolysis and more particularly to an electrolysis machine that provides for quick removal of hair.

2) Description of the Prior Art

Removal of unwanted hair on male and female humans has long been known. Removal of unwanted hair is usually accomplished by means of electrolysis. The prime objective of electrolysis is to permanently remove the hair after a single application. This is normally accomplished by destroying the hair follicle from which the hair grows. This destruction of the hair follicle is to be accomplished with a minimum amount of tissue destruction and also with a minimum amount of pain during application of the technique. Electrolysis is normally applied by means of an electrologist.

For a great many years, electrolysis used only direct current. The direct current tends to flow more quickly to areas where it is moist, namely the lower portion of the hair follicle.

This results in the producing of a chemical reaction, the main product of which is sodium hydroxide or lye. This sodium hydroxide is caustic and literally eats away at the hair.

Direct current electrolysis produces a low rate of regrowth of the hair which is quite advantageous. However, direct current has certain disadvantages in that it takes a substantial period of time (one to three minutes) for each hair follicle. Therefore, considering the wages of an electrologist, direct current electrolysis is quite expensive. Also, direct current electrolysis is somewhat painful to the patient.

In recent years, a new electrolysis technique, called "thermolysis" became prevalent. Thermolysis is used with a probe in the same manner as the direct current electrolysis uses a probe. However, with thermolysis, instead of direct current, a high frequency sinusoidal voltage is injected into the follicle. The radio frequency tends to physically cook the follicle thereby desiccating such.

Thermolysis has the primary advantage in that it is exceedingly fast and can be even faster than a tenth of a second for high intensity bursts of radio frequency energy. Thermolysis also has the advantage that it is simple to train an operator to understand the technique. Most often, thermolysis takes three to five seconds, which is an incredible increase over the one to three minutes, which is necessary with direct current electrolysis.

Thermolysis also has the additional advantage in that the heating pattern begins at the tip of the probe and spreads with time. This is called the "point affect" and causes the follicle destruction to begin at the very bottom, which is a desirable location to achieve complete follicle destruction. The disadvantage of thermolysis is that the heating pattern is narrow. It has been generally found that thermolysis has a low reliability factor when used on heavier curly hair. This is due to the fact that the heavy hair follicles are too wide for the heating pattern. In relation to curly hair, the follicle itself will curl away from the probe and thereby leave hair follicle areas which have not been destroyed. Any portion of the hair follicle that has not been destroyed will be capable of regrowing.

Within the last few years, a new technique came to pass which has been called the "blend technique." This blend technique combines a direct current technique with the radio frequency technique. The radio frequency technique causes heat in the follicle which increases the rate of chemical action for the direct current. The heat also tends to open the tissue allowing the lye to penetrate the tissue much more quickly. The result is reliability and low regrowth rates of the direct current technique has been obtained with a substantially shorter period of time.

Normal treatment time for the blend technique is between twenty and fifty seconds. This is considerably longer than the thermolysis technique by itself, but also substantially shorter than direct current electrolysis by itself. For discussion of the blend technique, reference is to be had to U.S. Pat. No. 4,598,709, entitled ELECTROLYSIS MACHINE, which has been issued to a Margaret M. Smith who is one of the inventors of the present application.

One of the disadvantages of the prior art electrolysis machines is that they use only a single probe. Inherently, there is a certain time that is required in order to effect destruction of the hair follicle. If only a single probe is used, then only a single hair follicle is being destroyed within that given period of time. If the electrolysis machine includes a plurality of probes, then the electrologist can use a plurality of probes within that same period of time thereby effecting removal of a plurality of hairs rather than a single hair. Therefore the use of a multi-probe machine is definitely more cost effective. Multi-probe electrolysis machines have generally been known in the prior art. However, these machines have only utilized direct current. It has not been known to utilize a multi-probe machine that uses both direct current and radio frequency.

Previous to the present invention, it has only been known to construct an electrolysis machine as a single unit which is locatable on a supporting surface such as a table or desk. The electrologist is constantly setting dials on the machine and referring to the meter or meters on the machine to insure that the correct voltage and current is being transmitted to the patient. It is desirable to have the machine maneuvered to be located directly in front of the electrologist during usage thereby making the machine readily observable as the electrologist works on the patient.

SUMMARY OF THE INVENTION

An electrolysis machine that is constructed of two separate units comprising a main unit and an arm unit. The main unit is to be positioned in a fixed location on a desk or table. The arm unit is to be mounted on an extendable adjustable arm which is to permit maneuverability of the arm unit to any desired position directly adjacent the electrologist and the patient. The arm unit has mounted thereon a plurality of probes with generally six in number being preferred. The circuitry within the electrolysis machine utilizes both direct current and radio frequency. The direct current is to be adjustable to different levels between zero and one milliamp. Radio frequency can be preset to a given level such as twenty-five volts, or can be adjustable to different levels. The electrologist is able to select only the direct current or can select the direct current combined with the radio frequency. Once a probe establishes contact with the patient, there is a short time period, such as a couple of seconds, to insure that the probe is then correctly positioned in conjunction with the hair follicle. The selected current is then transmitted to the probe for a preselected period of time which will generally be between twenty and fifty seconds. During the transmission of the electrical energy to this probe, the electrologist is able to install other probes to effect

3 removal of other hairs. When the first installed probe is deactivated, the electrologist can then remove that probe and then utilize it in conjunction with another hair follicle. Once the electrical circuit is established with the patient, the current transmitted to the patient is permitted to rise slowly over a two second time period to its preset level thereby minimizing the creation of any pain in using of the electrolysis machine of the present invention. The electrolysis machine can also be used as a skin conditioning apparatus since the circuitry includes an anaphoresis circuit and a cataphoresis circuit. When utilizing the electrolysis machine as a skin conditioning apparatus, probes are not used but instead a separate applying tool is connected directly to the main unit of the electrolysis machine.

The primary objective of the present invention is to construct an electrolysis machine which can be maneuvered to different positions so as to be readily accessible to an electrologist during usage with patient.

Another objective of the present invention is to construct an electrolysis machine which utilizes a plurality of probes which can be installed at the same time so as to effect removal of a plurality of hairs within the shortest period of time.

Another objective of the present invention is to construct an electrolysis machine which produces the level of current to the probe only upon the proper electrical connection being achieved by the probe.

BRIEF DESCRIPTION OF THE DRAWINGS

FIG. 9 is an electrical schematic for the direct current portion of the circuitry utilized in conjunction with each probe of the MULTI-PROBE BLEND ELECTROLYSIS MACHINE of this invention;

FIG. 10A is an electrical schematic for the radio frequency portion of the circuitry utilized in conjunction with probes 1, 2 and 3 mounted within the MULTI-PROBE BLEND ELECTROLYSIS MACHINE of this invention;

FIG. 10B is an electrical schematic for the radio frequency portion of the circuitry utilized in conjunction with

Figure 11:
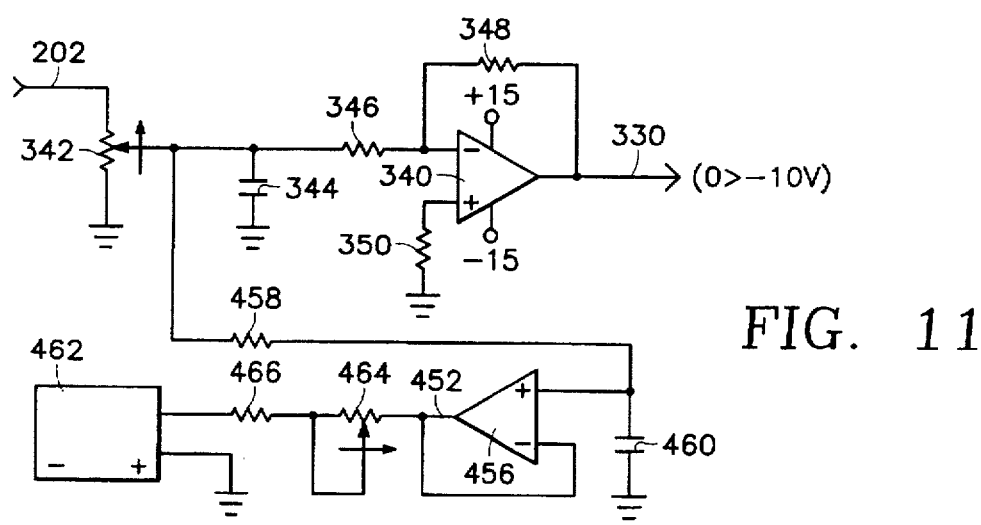
Figures 13, 14:
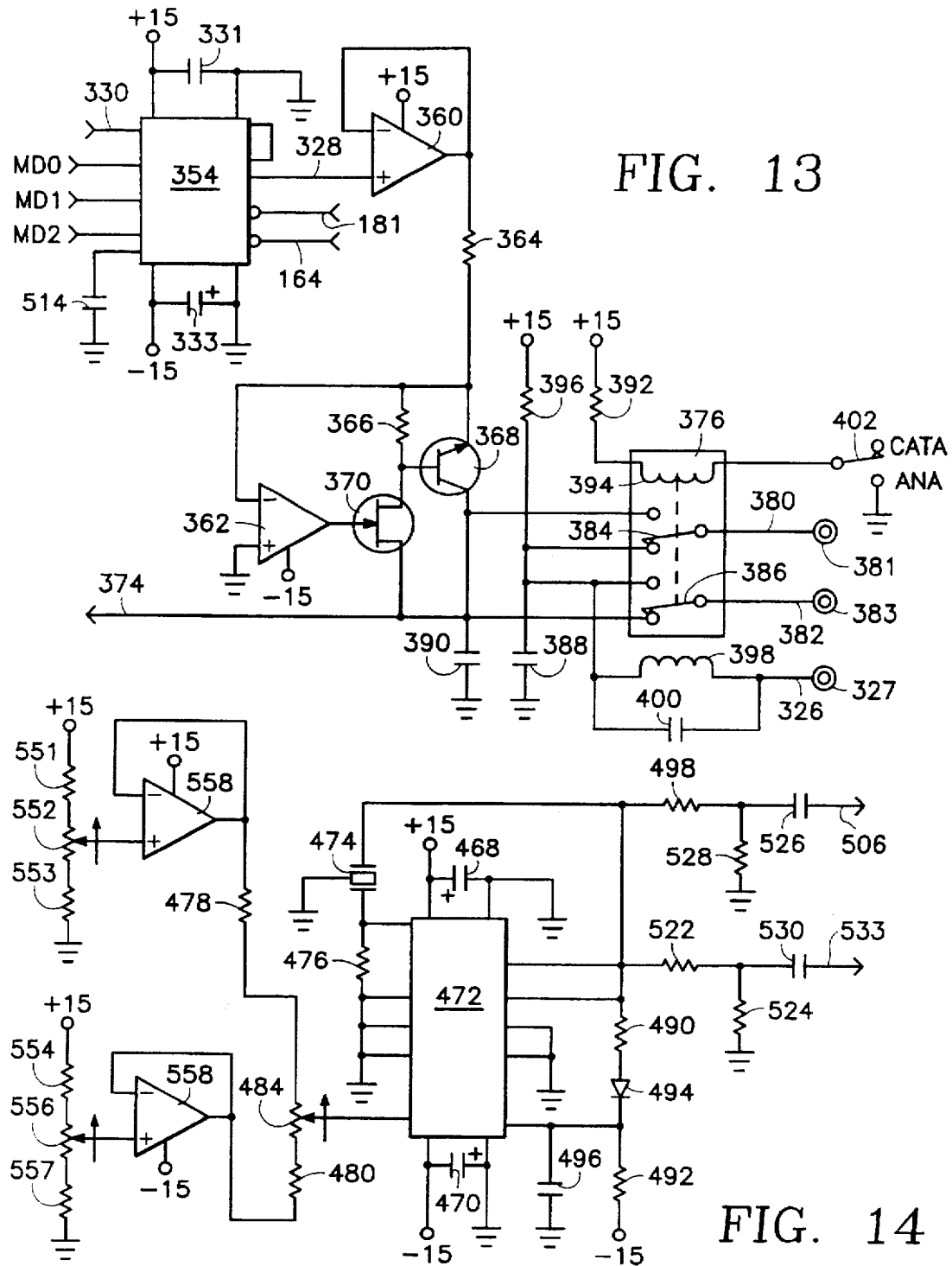

4 probes 4, 5 and 6 mounted within the MULTI-PROBE BLEND ELECTROLYSIS MACHINE of this invention;

FIG. 11 is an electrical schematic of a portion of the direct current circuitry that can be utilized to adjust the value of direct current that is transmitted to the patient;

FIG. 12 is an electrical schematic of a further portion of the control circuitry utilized in conjunction with the MULTI-PROBE BLEND ELECTROLYSIS MACHINE of this invention;

FIG. 13 is an electrical schematic of a further portion of the direct current control circuitry utilized within the MULTI-PROBE BLEND ELECTROLYSIS MACHINE of this invention; and FIG. 14 is an electrical schematic of a further portion of the radio frequency circuitry that is utilized in conjunction with the MULTI-PROBE BLEND ELECTROLYSIS MACHINE of this invention.

DETAILED DESCRIPTION OF THE PREFERRED EMBODIMENT

Figure 1:
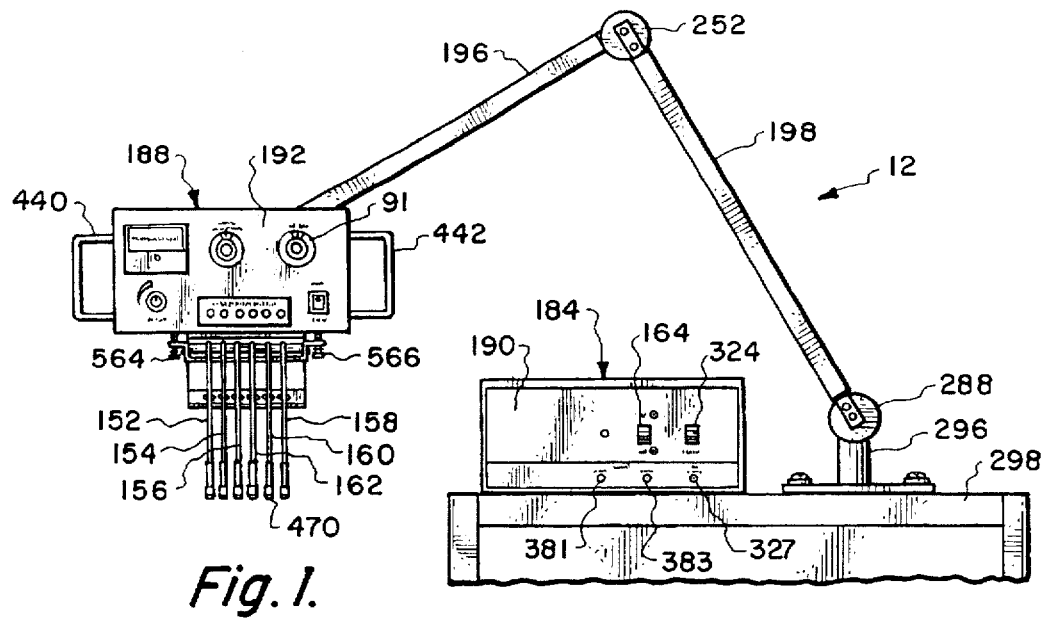
FIG. 1 is a front elevational view of the MULTI-PROBE BLEND ELECTROLYSIS MACHINE of this invention depicting a typical installation of the machine.
Figure 2:
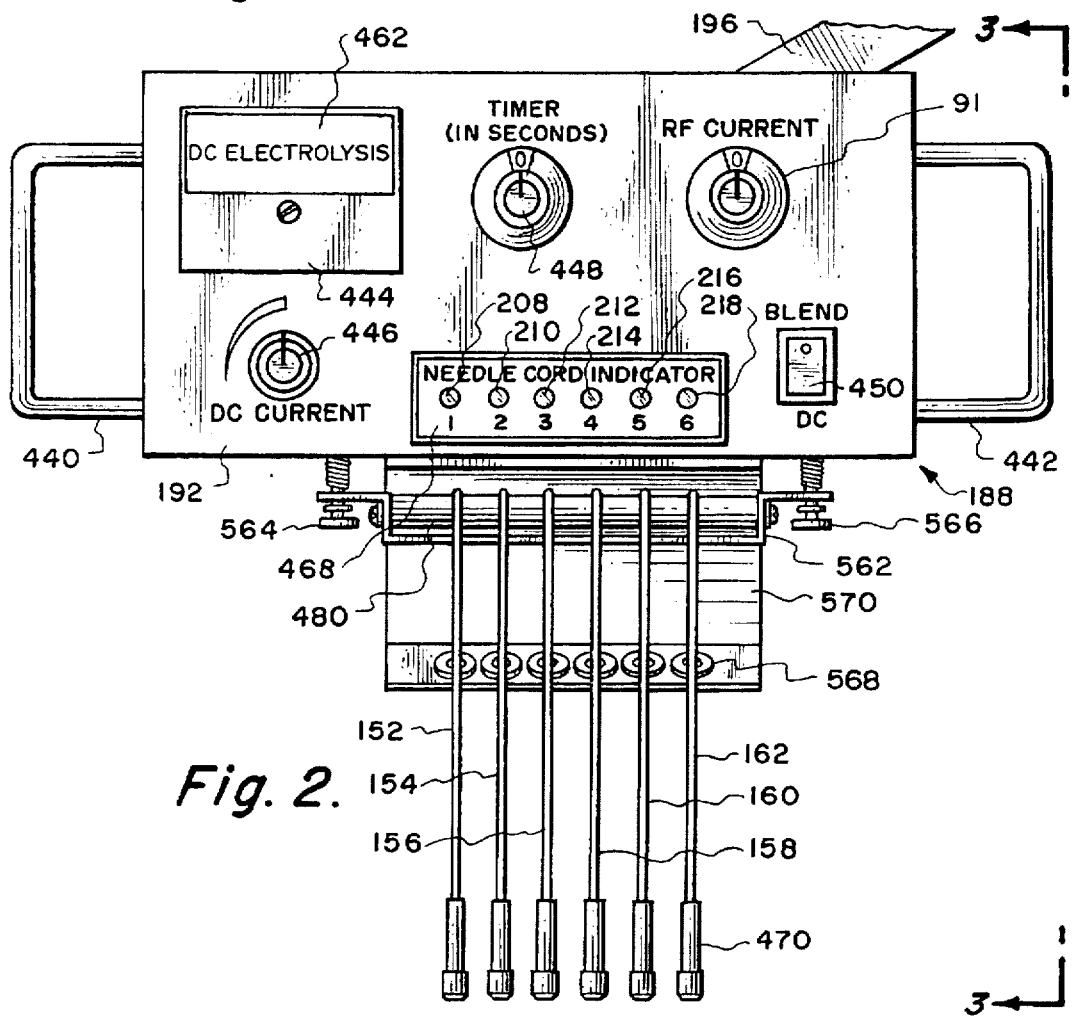
FIG. 2 is a front elevational view, enlarged in relation to FIG. 1, of the arm unit of the MULTI-PROBE BLEND ELECTROLYSIS MACHINE of this invention.
Figure 3:
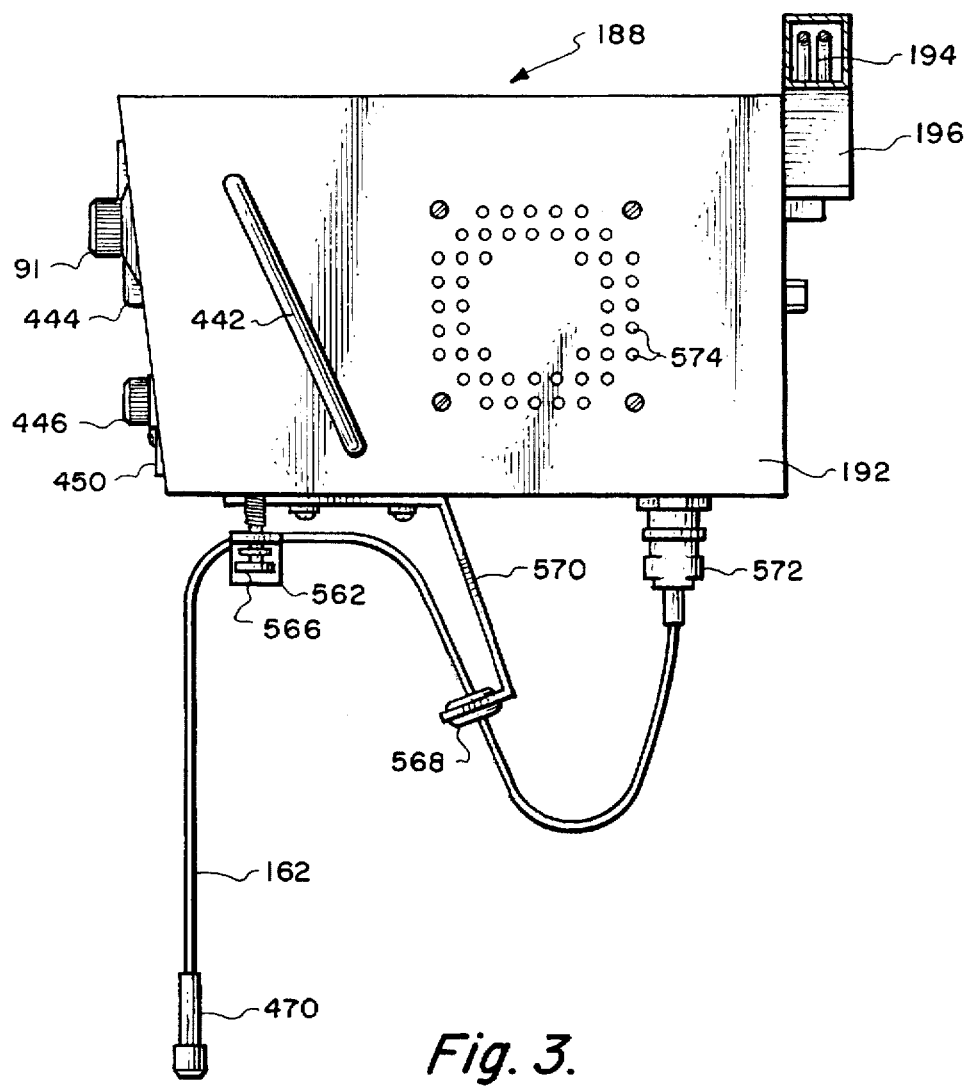
FIG. 3 is a side elevational view of the arm unit of the MULTI-PROBE BLEND ELECTROLYSIS MACHINE of this invention taken along line 3—3 of FIG. 2.
Figure 4:
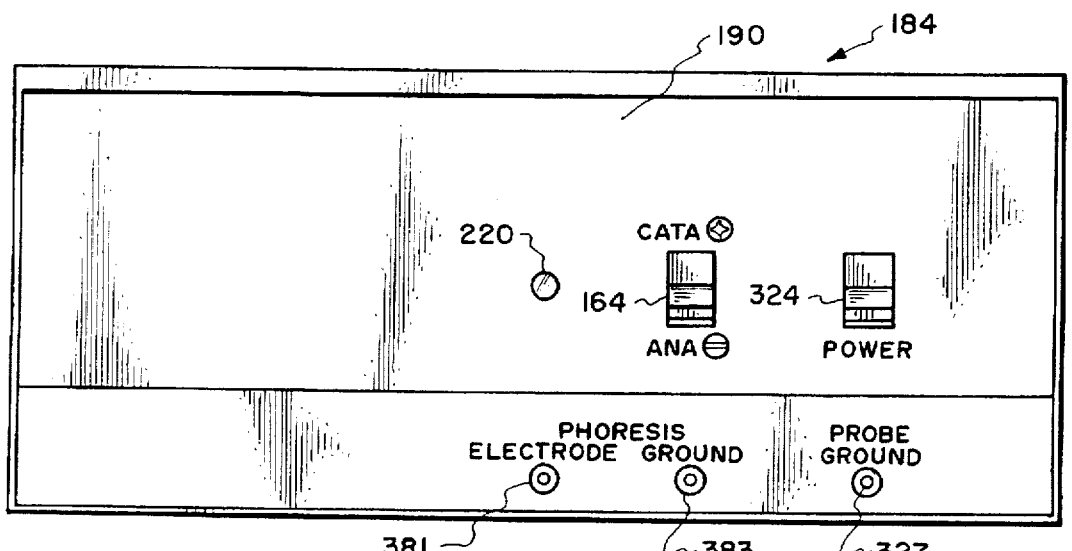
FIG. 4 is an enlarged view of the main unit of the MULTI-PROBE BLEND ELECTROLYSIS MACHINE of this invention.

Referring particularly to the drawings, there is shown in FIG. 1 a MULTI-PROBE BLEND ELECTROLYSIS MACHINE 12 of this invention. The MULTI-PROBE BLEND ELECTROLYSIS MACHINE 12 is composed of a main unit 184 and an arm unit 188. The main unit 184 is mounted within a rigid wall chassis 190 which is basically in the shape of a rectangular box. The arm unit 188 also is enclosed within a chassis 192 which is in the shape of a rectangular box. The appropriate electrical connection provided by electrical wires 194 are to connect to the main unit 184. The main unit 184 is to be connected to a source of electrical power which is not shown. The electrical wires 194 are mounted within and extend through arm members 196 and 198. Arm member 196 is pivotly connected to arm member 198 by means of a pivot joint 252. The arm member 198 is pivotly connected by means of a pivot joint 288 to a base mount 296. The base mount 296 is fixedly mounted onto a supportive surface such as a table 298. The main unit 184 is also shown mounted on the table 298.

The front panel of the chassis 190 of the main unit 184 has mounted therein jacks 327, 381 and 383. The jack 327 is to connect with an electrical wire (not shown). This wire will terminate in a grasping end which is to be electrically conductive. When the probe wires 152, 154, 156, 158, 160 and 162 are used to connect with the patient, that patient will also grasp the grasping end of the wire which connects to the jack 327. The jacks 381 and 383 are used solely for the purpose of conditioning of the skin. This conditioning is to be in the form of an electrically stimulating applicator (not shown) which is to be connected to the jack 381. An electrical wire (not shown), similar to the wire which connects to jack 327, is to be mounted in conjunction with the jack 383 and is to be held by the patient. The holding of the wire that connects to jack 383 will complete the circuit through the patient for the electrical stimulation. This electrical stimulation can be either in the form of a positive flow of current which is called cataphoresis or negative flow of current which is called anaphoresis. Selecting of anaphoresis or cataphoresis is strictly at the option of the electrologist and is selected by the electrologist depressing button 164 which connects to switch 402. Activation or turning on of the main unit 184 is accomplished by the electrologist depressing button 324 which closes switch 10.

Mounted on the chassis 192 of the arm unit 188 are a pair of handles 440 and 442. The handles 440 and 442 are to facilitate manual movement of the arm unit 188 to various different locations in close proximity to the main unit 184 but spaced therefrom. The pivot joints 252 and 288 of the arm members 196 and 198 are constructed so that when the arm unit 188 is released, it will remain in the released position and not move therefrom. The arm unit 188 is constructed to be relatively light in weight, generally no more than a few pounds in weight.

The front panel of the chassis 192 includes a DC meter panel 444. Within that DC meter panel 444 is the DC meter 462. This will inform the electrologist the amount of direct current that is being transmitted to the patient. The setting of the amount of the direct current between zero and one milliamp is to be selected by turning of the knob 446 which controls the direct current setting potentiometer 342. The amount of time that the current is to be applied to the patient is also to be selected in seconds by turning of the knob 448. Knob 448 operates the timing potentiometer 272. The operator also has the option of selecting only the direct current itself or direct current combined with radio frequency. In order to make this selection, the operator depresses button 450 which controls a mode switch 92. In one position of mode switch 92, the operator has selected direct current (DC) only and in the other position the operator has selected radio frequency (RF) combined with direct current (blend). When blend is selected, the operator can select the RF intensity by adjusting knob 91.

It is to be noted that mounted on the chassis 192 is a needle cord indicator box 468. Mounted within this needle cord indicator box 468 are the light emitting diodes 208, 210, 212, 214, 216 and 218. The number 1 is shown associated with light emitting diode 208, number 2 being associated with light emitting diode 210, number 3 being associated with light emitting diode 212, number 4 being associated with light emitting diode 214, number 5 being associated with light emitting diode 216 and number 6 being associated with light emitting diode 218. Aligning with the number 1 and light emitting diode 208 is probe wire 152. In a similar manner, probe wires 154, 156, 158, 160 and 162 align respectively with light emitting diodes 210, 212, 214, 216 and 218. Each of the probe wires 152, 154, 156, 158, 160 and 162 terminate in a needle (not shown) mounted within a tip 470. It is to be understood that the needle is to be inserted within the follicle of the hair. The probe wires 152, 154, 156, 158, 160 and 162 rest on a roller 480. The roller 480 is mounted on a bracket 562. The bracket 562 is mounted by means of screws 564 and 566 to the chassis 192. The roller 480 provides a low frictional surface for sliding of each of the probe wires 152, 154, 156, 158, 160 and 162 in an inward and outward direction relative to the arm unit 192.

Each of the probe wires 152, 154, 156, 158, 160 and 162 are mounted within a grommet 568 with it being understood that there is a separate grommet 568 for each of the probe wires 152, 154, 156, 158, 160 and 162. It is a function of each grommet 568 to provide a slight frictional resistance to its respective probe wires 152, 154, 156, 158, 160 and 162. The grommets 568 are mounted within a bracket 570 which is fixedly mounted onto the chassis 192. The inner end of each of the probe wires 152, 154, 156, 158, 160 and 162 are mounted by a probe connector 572 to the chassis 192.

It is to be noted that the probe wires 152, 154, 156, 158, 160 and 162 and the tips 470 as well as the needles (not shown) are referred to as probes within this patent application. Mounted within the chassis 192 are a series of ventilation holes 574 through which air is to be conducted in order to dissipate heat from the interior of the chassis 192. The chassis 192 of the arm unit 188 will also include ventilation holes.

Figures 5, 6:
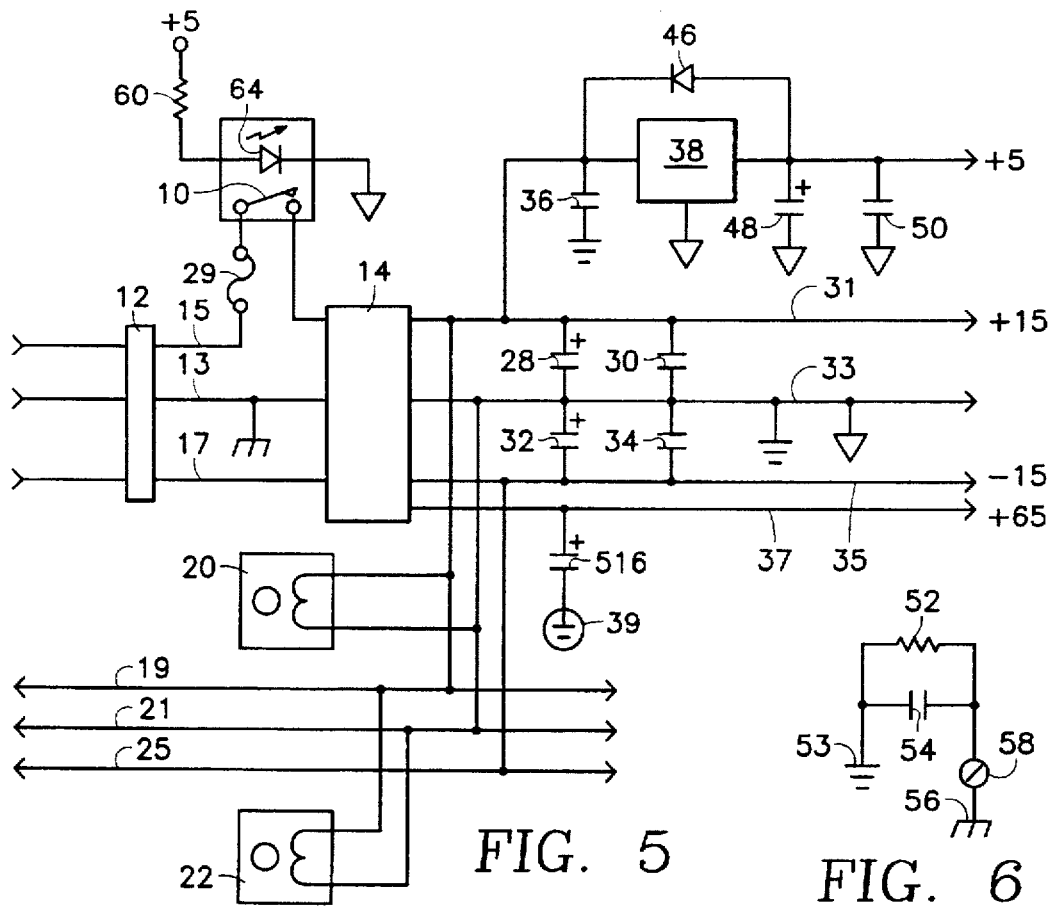
FIG. 5 is an electrical schematic of the power supply circuitry utilized in conjunction with the MULTI-PROBE BLEND ELECTROLYSIS MACHINE of this invention.
FIG. 6 is an electrical schematic of the electrical grounding of the chassis of the MULTI-PROBE BLEND ELECTROLYSIS MACHINE of this invention.

Referring specifically to FIG. 5, when the power switch 10 is turned on, alternating (AC) current flows through the connector 12 and through lines 15 and 17 to the power supply 14. Line 15 includes a fuse 29. Chassis ground line 13 also connects between connector 12 and power supply 14. The power supply 14 then supplies −15 volts direct current (VDC) through lines 31, 33 and 35 to fans 20 and 22. Fan 20 is mounted within the chassis of the main unit and functions to dissipate heat produced by the electronics. Fan 22 is mounted in the arm unit. Fan 22 is electrically connected to lines 19 and 21. Lines 19, 21 and 25 are to supply power (±15 volts) and electrical ground to the circuitry wherever this voltage is required. Line 19 is +15 volts, line 25 is −15 volts and line 21 is ground. Lines 19, 21 and 25 are also used to transmit power (±15 volts) to the DC PCB shown in FIGS. 9 and 13. From power supply 14 is a +65 VDC output line 37. Capacitor 516 connects line 37 to RF ground 39, capacitor 516 provides noise bypassing for the +65 VDC. RF ground is shown different than the common analog ground which is not specifically numbered throughout the circuits of the figures.

Figure 7A:
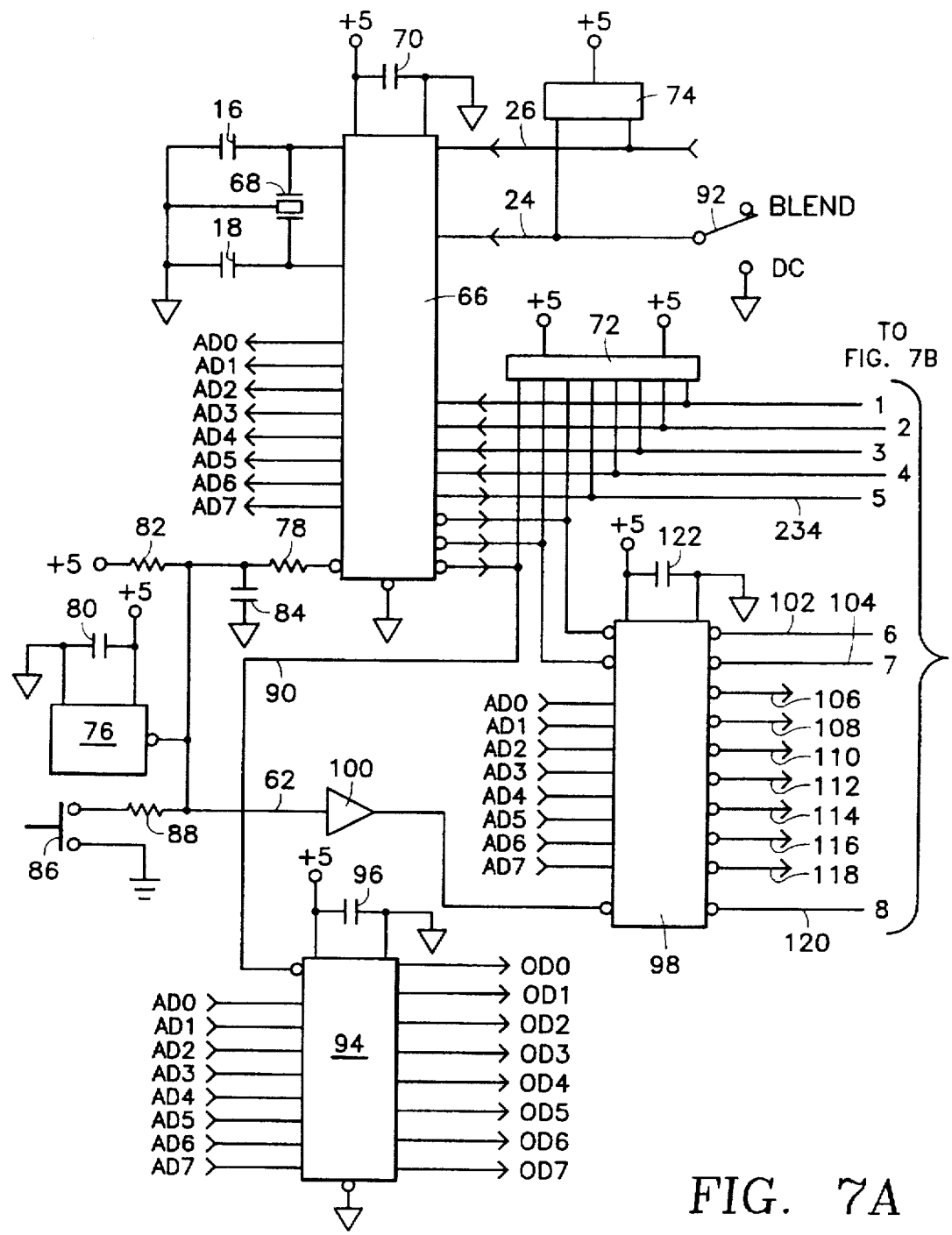
FIG. 7A and FIG. 7B constitute an electrical schematic of the control circuitry utilized in conjunction with the MULTI-PROBE BLEND ELECTROLYSIS MACHINE of this invention.
Figure 7B:
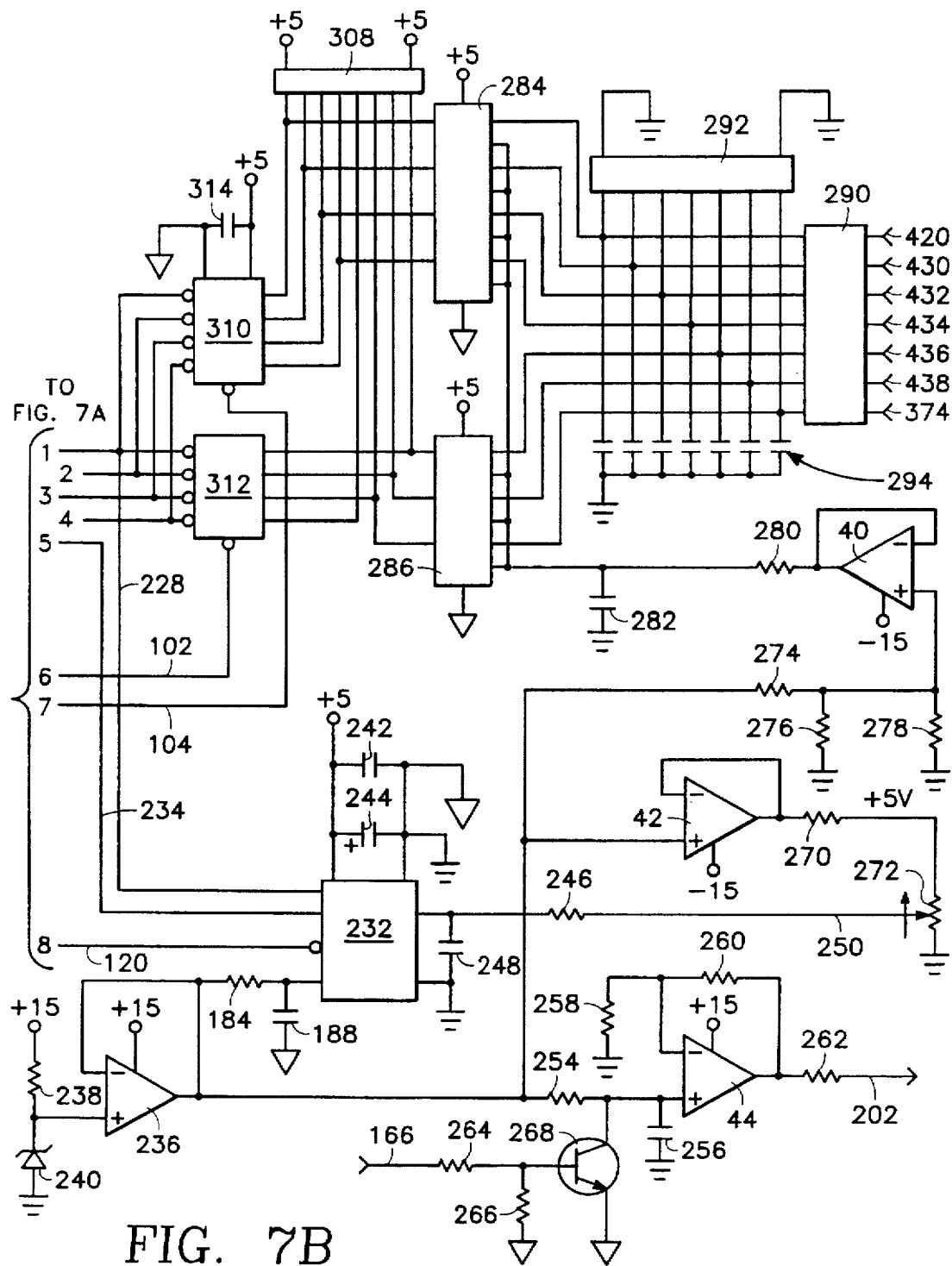
Figure 8:
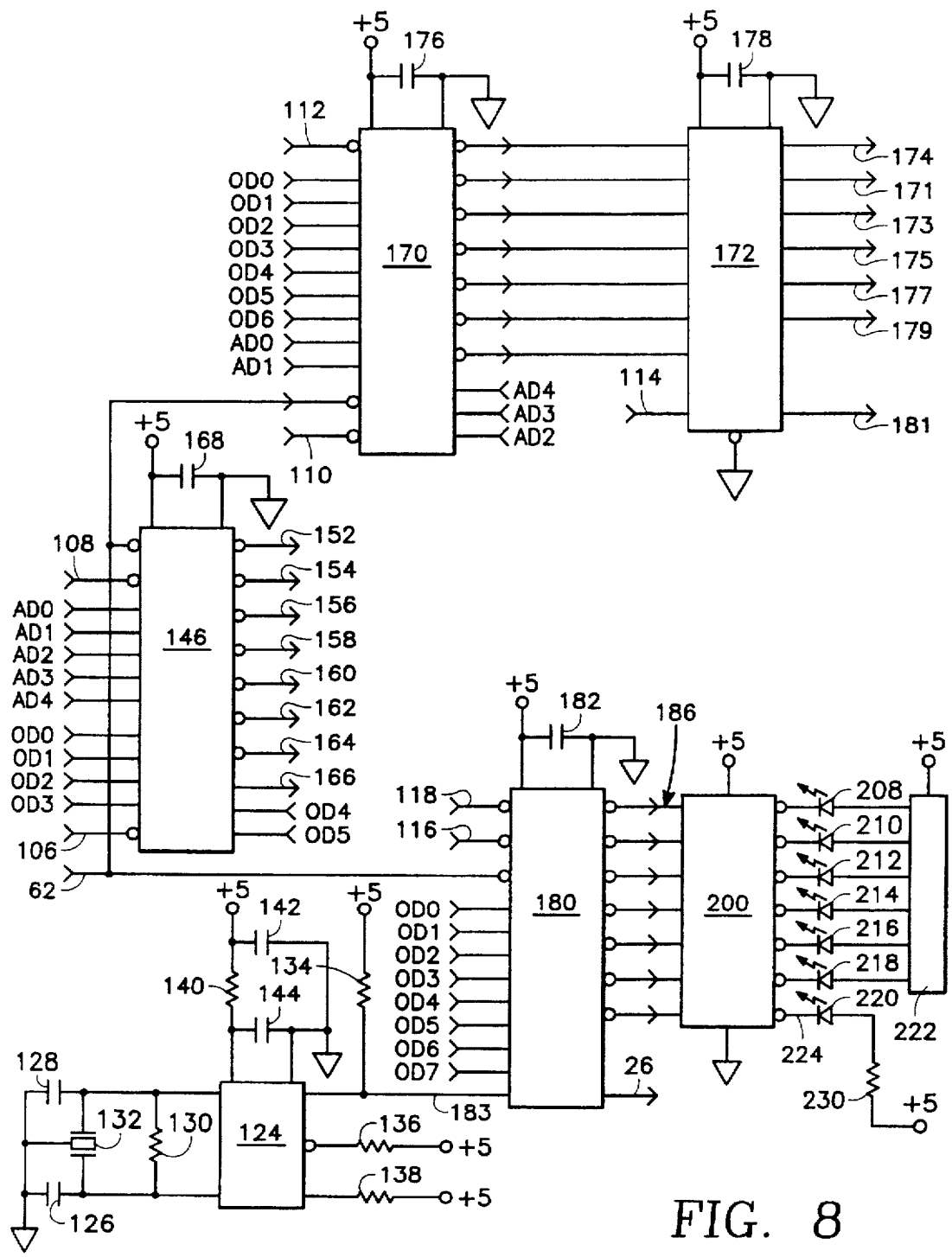
FIG. 8 is an electrical schematic of a further portion of the control circuitry utilized in conjunction with the MULTI-PROBE BLEND ELECTROLYSIS MACHINE of this invention.

Plus and minus (±) 15 VDC is supplied to the control PCB shown in FIGS. 7 and 8. Capacitors 28, 30, 32, 34 and 36 provide noise bypassing for the ±15 VDC. Five volt regulator 38 supplies 5 volt DC power to all the integrated circuits of the control PCB of FIGS. 7 and 8 except chips 40, 42, 44 and 236. Diode 46 provides over voltage protection for 5 volt regulator 38. Capacitors 48 and 50 provide noise bypassing for 5 volt regulator 38.

Between the chassis and the control PCB there is mounted resistor 52 which provides signal ground-to-chassis ground isolation shown in FIG. 6. Capacitor 54 provides signal ground noise bypassing between analog ground 53 and chassis ground 56. Mounting screw 58 mounts to chassis 190. Resistor 60 provides a voltage to turn on the light emitting diode (LED) 64 mounted in conjunction with the power switch 10.

The microcontroller integrated circuit 66 controls the total operation of the apparatus of this invention. A desirable microcontroller is Part No. P1C16C5X manufactured by Microchip Technology, Inc. Microcontroller 66 receives and sends data, address (ADO to AD7) and control signals. Microcontroller 66 operates from a 4 megahertz (MHz) resonator 68 which operates between capacitors 16 and 18. Capacitor 70 is a 5 VDC bypass capacitor for microcontroller 66. Five VDC pull up resistor arrays 72 and 74 are operatively connected to microcontroller 66. Chip 76 is a supervisory chip that supervises microcontroller 66 by monitoring the power supply 14 and providing system resets through resistor 78. Capacitor 80 is a 5 VDC bypass capacitor for the supervisory chip 76. Resistor 82 is a 5 VDC pull up resistor and capacitor 84 is a noise bypass capacitor. A reset switch 86 operates through resistor 88 to provide a way to do a master reset of the whole system of this invention putting the system at the start point. Lines 24 and 26, which connect to resistor array 74, connect microcontroller 66 to mode switch 92 which informs microcontroller 66 if the system is in a single or dual current operation mode. The single mode would be DC only and the dual mode would be radio frequency RF and DC. Line 26 supplies a signal received from chip 180.

Chip 94 is an octal D-type flip-flop that receives address signals (ADO–AD7) from microcontroller 66 and sends out data signals (ODO–OD7). A desirable octal D-type flip-flop is manufactured by National Semiconductor, Part No. 54AC/74AC574. The capacitor 96 is a 5 VDC bypass capacitor for chip 94. The control signal from microcontroller 66 is also transmitted through line 90 to chip 94.

Chip 98 is a programmable logic array that receives address signals (AD0–AD7) and control signals from microcontroller 66. The control signal through line 62 includes buffer 100. A desirable logic array would be Part No. 22CV10A, manufactured by ICT, Inc. Chip 98 sends out chip select, latch, control and IO (in/out) write signals in lines 102, 104, 106, 108, 110, 112, 114, 116, 118 and 120. Line 102 connects to chip 312. Line 104 connects to chip 310. Lines 106 and 108 connect to chip 146. Lines 110 and 112 connect to chip 170. Line 114 connects to chip 172. Lines 116 and 118 connect to chip 180. Line 120 connects to chip 232. The capacitor 122 is a 5 VDC bypass capacitor for chip 98.

Chip 124 shown in FIG. 8 is an oscillator/divider that provides a 5 hertz (Hz) frequency operating system. Capacitors 126 and 128, resistor 130 and 6.55 megahertz (MHz) resonator 132 provide an operating frequency for chip 124. Resistors 134, 136 and 138 are 5 VDC pull up resistors. Resistor 140 is a 5 VDC isolation resistor. Capacitor 142 is a 5 VDC bypass capacitor for resistor 140. Capacitor 144 is an isolated 5 VDC bypass capacitor for chip 124.

Chip 146 is a programmable logic array that receives address signals (AD0-AD4) from microcontroller 66 and control signals from programmable logic array 98 through lines 106 and 108. Chip 146 also receives data signals (OD0–OD5) from octal D-type flip flop 94. Chip 146 sends out DC chip select and 10 V reference control signals in lines 152, 154, 156, 158, 160, 162, 164 and 166. Line 152 connects to chip 404 of FIG. 9. Each of the lines 154, 156, 158, 160 and 162 connect respectively in an identical manner to a chip (not shown) that is identical to chip 404. Capacitor 168 is a 5 VDC bypass capacitor for chip 146.

Chip 170 is a programmable logic array that receives address signals (OD0-OD6) from octal D-type flip flop 94, control signals from programmable logic array 98 through lines 110 and 112, and address signals (AD0–AD4) from microcontroller 66. Chip 170 sends out RF disable signals that are buffered by chip 172 which is an octal non-inverting buffer. Capacitor 176 is a 5 VDC bypass capacitor for chip 170. Capacitor 178 is the same for chip 172. The RF disable signal in line 174 from chip 172 is transmitted to feedback amplifier 500 for probe number one. The output signals in lines 171, 173, 175, 177 and 179 are each to be transmitted to a separate RF circuit (not shown) each of which is basically identical to the RF circuit shown in FIG. 10. Chip 172 produces a write signal in line 181 that is transmitted to chip 404 as well as the other not shown five in number of similar circuits. Line 181 is also transmitted to chip 354.

Chip 180 is a programmable logic array that receives data signals (OD0-OD7) from chip 94 as well as the control signals from chips 98 and 100, and a 5 Hz signal in line 183 from chip 124. Capacitor 182 is a 5 VDC bypass capacitor for chip 180. Chip 180 sends out a buffered 5 Hz signal in line 26 and a series of LED signals in lines 186. The LED signals in lines 186 are transmitted to chip 200 which is a 5 volt collector driver. From chip 200 there are six outputs each of which connect to a single LED 208, 210, 212, 214, 216 and 218 which are connected to a 5 VDC pull up resistor array 222. The LED signal in line 224 is transmitted to LED 220. LED 220 indicates to the user that the circuit is either in the cataphoresis mode or the anaphoresis mode. Resistor 230 is a pull up resistor for LED 220.

Chip 232 is an analog-to-digital converter. Chip 232 receives control, clock, 5 volt reference and timer set signals from line 120 of chip 98 and from line 234 from microcontroller 66. Chip 232 sends out a digital voltage to microcontroller 66 in line 228. Capacitors 242 and 244 are 5 VDC bypass capacitors for chip 232. Resistor 246 and capacitor 248 comprise a filtering circuit for the timer pot signal of timer potentiometer 272 in line 250 from chip 232.

Chips 236, 40, 42 and 44 are each operational amplifiers that supply a buffered 0.36 volts, 5 and 10 volt reference voltages. Resistor 238 and diode 240 provide a 5 VDC reference voltage signal to chip 236. Chip 236 provides a 5 VDC buffered reference voltage to chips 40, 42, 44 and through resistor 184 and filtering capacitor 188 to chip 232. Resistor 254 and capacitor 256 comprise a filtering circuit for chip 44. Resistors 258 and 260 in connection with chip 44 provide a buffered 10 VDC reference signal in line 202 through resistor 262 which is supplied to DC potentiometer 342 in FIG. 11. Resistor 262 is a short circuit protection and noise reduction resistor. Resistors 264 and 266 along with transistor 268 are used to turn off the 10 VDC signal. Resistor 264 is mounted in line 166 which is an output of chip 146. Chip 42 provides a buffered 5 volt reference signal that goes through resistor 270 to the timer potentiometer 272. Resistor 270 is a short circuit protection and noise reduction resistor. Resistors 274 and 276 plus chip 40 and the 866 ohm resistor 278 provide a buffered 0.36 volt reference signal that goes through the filtering network of resistor 280 and capacitor 282 to chips 284 and 286. Chips 284 and 286 are quad comparators that receive a 0.36 reference voltage and DC analog signals. The DC analog signals are sent through a resistor array divider circuit to chips 284 and 286. The resistor array divider circuit is formed by resistor arrays 290 and 292. Capacitors 294 are bypass capacitors. Chips 284 and 286 send out zero or 5 volt logic signals which are transmitted to 5 volt pull up resistor array 308. The outputs from chip 284 coupled with the resistor array 308 are transmitted to chip 310 of an octal inverting buffer. In the same way, the outputs from chip 286 that have been coupled with resistor array 308 are transmitted to chip 312 which is also part of the octal inverting buffer. The octal inverting buffer, composed of chips 310 and 312, receives the logic signals from chips 284 and 286 and sends such to the microcontroller 66. Capacitor 314 is a 5 VDC bypass capacitor for the octal inverting buffer composed of chips 310 and 312.

Referring specifically to FIG. 11, chip 340 comprises a dual operational amplifier that receives DC voltage from the DC set potentiometer 342. Capacitor 344 is a filtering capacitor. Resistors 346, 348 and 350 provide a buffered negative DC voltage. The output of chip 340 in line 330 is transmitted to chip 404 for probe one and also for the identical circuits (not shown) for probes two through six. The output in line 330 is also supplied to chip 354 as well as control signals MD0, MD1 and MD2 from chip 356.

Chip 354 of FIG. 13 is a digital attenuator that receives control signals (MD0, MD1 and MD2) from chip 356. Chip 356 is an octal non-inverting buffer. Part No. 54AC/74AC244, manufactured by National Semiconductor, would be satisfactory. Capacitor 357 is a noise bypassing capacitor for chip 356. Chip 354 sends out a negative DC voltage in line 328 that digitally ramps from 0 to 100 percent in two seconds (20 percent, 50 percent, 80 percent, 100 percent in half-second intervals) to amplifier 360. Capacitor 514 helps slow the ramping and eliminate the sudden heat sensation that is felt by the user. Capacitors 331 and 333 are noise bypassing capacitors for chip 354. Amplifier 360 is one-half of a dual operational amplifier which includes amplifier 362. Amplifier 360 receives a negative DC voltage from chip 354 and buffers it before it is transmitted through resistor 364 to amplifier 362. Amplifier 362, resistor 366, transistors 368 and 370 create a constant direct current source signal that goes to resistor array 290 through line 374 (FIG. 7). Line 374 also connects with a 12 VDC relay 376. Line 374 connects to both lines 380 and 382 which are outputs from the relay 376. Line 380 connects with relay switch 384 with line 382 connecting with relay switch 386. Capacitors 388 and 390 are filtering capacitors. Resistor 392 provides a voltage to the coil 394 of the relay 376. Resistor 396 provides a voltage source to the inductor 398 and capacitor 400 and to switches 384 and 386. Inductor 398 and capacitor 400 are connected to the probe ground line 326 which connects to jack 327 for the probes one through six. Line 380 outputs to jack 381. Line 382 outputs to jack 383. A signal from switch 402 causes the relay 376 to change the position of switches 384 and 386. Switch 402 is to either select cataphoresis or anaphoresis.

Chip 404 is a digital attenuator that receives control signals (MDO, MD1 and MD2) from chip 356 of FIG. 12. Also, a negative DC set voltage is transmitted to chip 404 from line 330 which is the output of chip 340. It is to be understood that the circuits (not shown) for probes two through six, which are essentially identical to FIG. 9, are also to receive control signals MDO, MD1 and MD2 as well as a negative DC set voltage from line 330. Chip 404 sends out a negative DC voltage that digitally ramps from 0–100 percent in two seconds (20 percent, 50 percent, eighty percent in half-second intervals) to chip 406. Capacitors 408 and 410 are noise bypassing capacitors for chip 404. Capacitor 512 helps slow the ramping and eliminate the sudden heat sensation that is felt by the user.

Chip 406 is a dual operational amplifier in conjunction with chip 412. Chip 406 receives a negative DC voltage from chip 404 and buffers this signal through resistor 414 to chip 412. Chip 412, resistor 413 and transistors 416 and 418 create a constant current source signal within line 420 that is transmitted to resistor array 290. The direct current output of chip 412 is also transmitted through resistor 422 in line 421 to the circuit of FIG. 10. Resistor 422 is a short circuit protection and noise reduction resistor. Capacitor 424 is a filtering capacitor. It is to be understood that there are a total of six in number of circuits that are shown in FIG. 9. There is to be a circuit shown in FIG. 9 for each probe one through six. The output in line 420 is transmitted to the circuit for probe one (FIG. 9). The output of a similar circuit is transmitted to the circuit by probe two similar to FIG. 10 and so forth up to probe six. The output signals of each of these circuits of probe two through six are transmitted respectively through lines 430, 432, 434, 436 and 438 to resistor array 290.

Plus and minus 15 volts DC from lines 31, 33 and 35 and +65 VDC from line 37 are supplied to the RF circuit shown in FIG. 10. Chip 456 in FIG. 11 is a dual operational amplifier that receives a DC voltage from the DC set potentiometer 342 through resistor 458. Capacitor 460 is a filter capacitor. Chip 456 sends out a buffered DC voltage through line 452 to the DC meter 462 through the trim potentiometer 464 and resistor 466.

Chip 558 is a dual operational amplifier. One half of chip 558 is a buffer for the DC voltage from the divider circuit of resistors 551 and 553 and trim potentiometer 552. Trim potentiometer 552 is used to set the high end (40 VP-P) of the RF output. The other half of chip 556 is a buffer for the DC voltage from the divider circuit of resistors 554 and 557 and trim potentiometer 556. Trim potentiometer 556 is used to set the low end (30 VP-P) of the RF output. Resistors 478 and 480 provide noise reduction to the RF potentiometer 484. The RF potentiometer 484 is used to adjust the RF output at the patient from 30 VP-P to 40VP-P.

Chip 472 in FIG. 14 is a wideband, variable gain amplifier that receives a frequency from the 13.56 MHz crystal 474 and resistor 476. A typical wideband, variable gain amplifier would be part no. EL4551C manufactured by ELANTEC. Capacitors 468 and 470 are bypass capacitors. Resistors 490 and 492, diode 494 and capacitor 496 form a feedback circuit to chip 472 for balancing the RF output signal. The RF output signal goes to two separate resistor divider circuits. The signal from RF potentiometer 484 goes through the noise filtering circuit of resistor 482 and capacitor 518.

The RF output from chip 472 goes to two gain circuits. Resistors 498 and 528 form one RF gain circuit. Resistors 522 and 524 form the other gain circuit. Capacitor 526 is an AC coupling capacitor that goes to probes 1, 2 and 3. Capacitor 522 is an AC coupling capacitor that goes to the probes 4, 5 and 6.

Chip 500 is connected to probe number 1. Separate circuits similar to FIG. 10A will be used for probe number 2 and probe number 3. Chip 500 is 110 MHz current feedback amplifier with disable that receives an RF disable signal in line 174. Part No. EL2155C of ELANTEC is a satisfactory part for this purpose. Chip 500 also receives the output signal of line 506 from capacitor 526. It is to be understood that each of the circuits similar to FIG. 10A for probes two and three will also receive the signal of line 506. Resistors 508 and 510 cause chip 500 to amplify the radio frequency signal by a factor of two. Capacitor 520 is an AC coupling capacitor.

Chip 538 is a triple 80 MHz CRT driver that receives the amplified RF signal from capacitor 520 through the gain resistor 521. For chip 538 part No. LM2427T manufactured by National Semiconductor would be a satisfactory part for this purpose. Chip 538 is also grounded by RF ground 539. Probe 1 is also grounded by RF ground 541. Resistor 531 cause chip 538 to amplify the RF signal by a factor of −13. The output of chip 538 goes through the impedance resistor 532. Capacitor 540 is an AC coupling capacitor that allows the RF current source signal from resistor 532 to be transmitted to probe 1. It is to be kept in mind that there are six in number of different probes. The constant DC source signal in line 544 is conducted through the AC filtering circuit composed of inductor 546 and capacitors 548 and 550 to probe 1.

Referring now to Figure 10B, there is shown a circuit for probe 4 with similar separate circuits to be used for probes 5 and 6. Chip 562 is connected to probe number 4. Chip 562 is a 110 MHz current feedback amplifier with disable that receives an RF disable signal from line 175. Chip 562 also receives the output signal of line 533 from capacitor 530. It is to be understood that each of the circuits similar to Figure 10B for probes 5 and 6 will also receive the signal of line 533. Resistors 560 and 561 cause chip 562 to amplify the radio frequency signal by a factor of two. Capacitor 563 is an AC coupling capacitor.

Chip 565 is a triple 80 MHz CRT driver that receives the amplified RF signal from capacitor 563 through the gain resistor 564. Resistor 564 causes chip 565 to amplify the RF signal by a factor of −13. Chip 565 is also grounded by RF ground 572. Probe 4 is also grounded by RF ground 573. The output of chip 565 goes through the impedance resistor 566. Capacitor 567 is an AC coupling capacitor that allows the RF current source signal from resistor 566 to be transmitted to probe 4. The constant DC source signal in line 544 is conducted through the AC filtering circuit composed of inductor 569 and capacitors 570 and 571 to probe 4.

What is claimed is:

1. An electrolysis machine comprising:

a main unit containing first electronic components, said main unit being fixedly located on a supporting surface; and an arm unit having an outer end and an inner end, said arm unit permitting movement of said outer end relative to said inner end and said main unit, said inner end being fixable to said supporting surface, said outer end being free, a chassis mounted on said outer end, said chassis containing second electronic components, a plurality of probes mounted on said chassis, said probes electrically connecting with said electronic components, each said probe to be usable to connect with a hair follicle to effect removal of hair, said chassis having protruding handle means, said handle means being graspable permitting manual adjusting movement of said chassis to said arm unit relative to said supporting surface.

2. The electrolysis machine as defined in claim 1 wherein:

said first electronic components and said second electronic components including a direct current circuit and a radio frequency circuit.

3. The electrolysis machine as defined in claim 2 wherein:

said first electronic components and said second electronic components also including an anaphoresis circuit and a cataphoresis circuit.

4. The electrolysis machine as defined in claim 3 wherein:

said anaphoresis circuit and said cataphoresis circuit each having a current level, said current level for both said anaphoresis circuit and said cataphoresis circuit being identical, said current level slowly rising over a two second time period upon the establishment of either said anaphoresis circuit or said cataphoresis circuit.

5. The electrolysis machine as defined in claim 2 wherein:

the operating current level of said direct current circuit being adjustable prior to usage of a said probe.

6. The electrolysis machine as defined in claim 1 wherein:

said handle means comprising a pair of spaced apart handles mounted on said chassis.

* * * * *